US008725245B2

(12) United States Patent
Feldkamp et al.

(10) Patent No.: US 8,725,245 B2
(45) Date of Patent: May 13, 2014

(54) RESONANT COIL FOR MEASURING SPECIMEN CONDITION

(75) Inventors: Joseph R. Feldkamp, Appleton, WI (US); Jeffrey R. Heller, Neenah, WI (US); Shawn J. Sullivan, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1676 days.

(21) Appl. No.: 11/464,284

(22) Filed: Aug. 14, 2006

(65) Prior Publication Data

US 2008/0048786 A1     Feb. 28, 2008

(51) Int. Cl.
   *A61B 5/05*           (2006.01)
   *G01R 27/08*       (2006.01)

(52) U.S. Cl.
USPC .......................... 600/547; 324/691; 324/692

(58) Field of Classification Search
USPC ................................... 600/547; 324/691, 692
See application file for complete search history.

(56) References Cited

U.S. PATENT DOCUMENTS

| | | | | |
|---|---|---|---|---|
| 4,114,606 A | * | 9/1978 | Seylar | 600/409 |
| 4,116,231 A | * | 9/1978 | Matsuo | 600/547 |
| 4,433,693 A | * | 2/1984 | Hochstein | 600/534 |
| 4,727,330 A | * | 2/1988 | Funk | 324/445 |
| 5,400,236 A | * | 3/1995 | Shimizu et al. | 363/37 |
| 5,722,997 A | * | 3/1998 | Nedungadi et al. | 607/28 |
| 6,147,881 A | * | 11/2000 | Lau | 363/17 |
| 7,241,630 B2 | | 7/2007 | Hawkins et al. | |
| 7,515,012 B2 | * | 4/2009 | Schulman et al. | 333/17.1 |
| 2006/0005845 A1 | * | 1/2006 | Karr et al. | 128/897 |
| 2006/0033500 A1 | * | 2/2006 | Wang et al. | 324/322 |

FOREIGN PATENT DOCUMENTS

| | | |
|---|---|---|
| EP | 1264746 A2 | 5/2002 |
| EP | 1611841 A1 | 4/2006 |
| GB | 1320403 | 6/1970 |
| JP | 63500567 A | 1/1987 |
| JP | 64057163 A | 3/1989 |
| JP | 63131095 A | 11/2001 |
| JP | 2001311750 A | 11/2001 |
| JP | 2002005892 A | 1/2002 |
| WO | 8700025 A1 | 1/1987 |

OTHER PUBLICATIONS

International Search Report and Written Opinion for PCT/IB2007/052904, dated Mar. 27, 2008, 13 pages.

(Continued)

*Primary Examiner* — Sean Dougherty
*Assistant Examiner* — Devin Henson
(74) *Attorney, Agent, or Firm* — Armstrong Teasdale LLP (57) ABSTRACT

An oscillator provides a reference signal having a phase. A tunable reactive circuit, including an induction coil, is driven by the fixed frequency reference signal of the oscillator with coil adapted to be positioned adjacent the specimen to generate an oscillating signal corresponding to the condition of the specimen. The tunable reactive circuit provides an output signal having a parameter indicative of the condition of the specimen. A resonant control circuit compares the reference signal to the oscillating signal and provides to the tunable reactive circuit a resonance control signal representative of the comparison. The resonance control signal tunes the tunable reactive circuit, which may be a series RLC circuit, so that the frequency of the oscillating signal is substantially constant.

19 Claims, 5 Drawing Sheets

(56) References Cited

OTHER PUBLICATIONS

Hart, L., et al., "A Noninvasive Electromagnetic Conductivity Sensor for Biomedical Applications," IEEE Transactions on Biomedical Engineering, Dec. 12, 1988, vol. 35, No. 12, pp. 1011-1022.

Guardo, R., et al., "Contactless Measurement of Thoracic Conductivity Changes by Magnetic Induction," Proceedings—19th International Conference—IEEE/EMBS, Oct. 30-Nov. 2, 1997, pp. 2450-2453, Chicago, Illinois, USA.

Roby, D., "A Comparison of Two Noninvasive Techniques to Measure Total Body Lipid in Live Birds," The Auk, Cooperative Wildlife Research Laboratory and Department of Zoology, Southern Illinois University, Jul. 1991, vol. 108, pp. 509-518, Carbondale, Illinois.

Harpen, M., et al., "Influence of Skin Depth on NMR Coil Impedance. Part II," Physics in Medicine & Biology, May 1988, vol. 33, No. 5, pp. 597-605, IOP Publishing Ltd, United Kingdom.

Analog Devices, Inc., "1 MSPS, 12-Bit Impedance Converter, Network Analyzer AD5933," product brochure, 2005, pp. 1-32, Norwood, Massachusetts.

Reimann, R. et al., "Nuclear Magnetic Resonance Field Discriminator Using Digital Techniques," Journal of Applied Mathematics and Physics, 1967, pp. 549-556, vol. 18, Switzerland.

Grounds for Rejection received in Japanese Application No. 2009-524260, mailed May 28, 2013.

* cited by examiner

United States Patent US 8,725,245 B2

RESONANT COIL FOR MEASURING SPECIMEN CONDITION

FIELD OF THE INVENTION

The present invention generally relates to conductivity measurements and, in particular, determining a condition of a specimen by noninvasive measurement of its conductivity.

BACKGROUND OF THE INVENTION

Measurement of conductivity for most liquids or solids involves the use of electrodes which are placed into contact with the specimen of interest. A voltage is applied (usually AC) with resulting current measured and conductivity computed. In some cases, many electrodes are attached so that a kind of imaging is made possible, provided that conductivity varies spatially through the specimen. This latter condition is true for geological specimens and human tissue specimens.

An alternative is to generate eddy currents within the specimen through inductive coupling to an external coil. The eddy currents exist in proportion to the local conductivity of the material and can be detected in a number of ways. A recent technique in connection with attempting to measure conductivity of the human thorax, more specifically cardiac output, measures the additional electrical energy dissipated in the coil when placed near to the patient's body.

In spite of techniques employed to date, various technical issues prevent widespread use: not well known or understood; competing invasive methods; inadequate development of models to distinguish the variety of factors contributing to human tissue conductivity, making interpretation less straightforward; and use of either expensive or awkward instrumentation to measure coil related parameters such as complex impedance. Many devices use circuitry that permits the frequency of the exciting voltage to vary as a coil is placed adjacent its target material. Such an arrangement makes interpretation of measurements more confusing.

SUMMARY OF THE INVENTION

A noninvasive induction type sensor measures electrical conductivity at some depth beneath the skin, and without the usual attachment of electrodes to the skin surface. In one embodiment, an induction coil forms part of an RLC autoresonant circuit that is forced to remain in resonance by a varactor diode combined with phase-locked loop circuitry. With such an arrangement, impedance of the resonant circuit and thus tissue conductivity is straightforward to measure, leading to compact electronics. A number of applications are contemplated, including an ability to monitor recovery from hypothermia, onset of hyperthermia, impairment of blood circulation or other circulator performance, cardiovascular elasticity, cardiac output, arterial dilation, edema, and fat distribution.

Other objects and features will be in part apparent and in part pointed out hereinafter.

BRIEF DESCRIPTION OF THE DRAWINGS

Corresponding reference characters indicate corresponding parts throughout the drawings.

DESCRIPTION OF THE PREFERRED EMBODIMENTS

Figure 1:
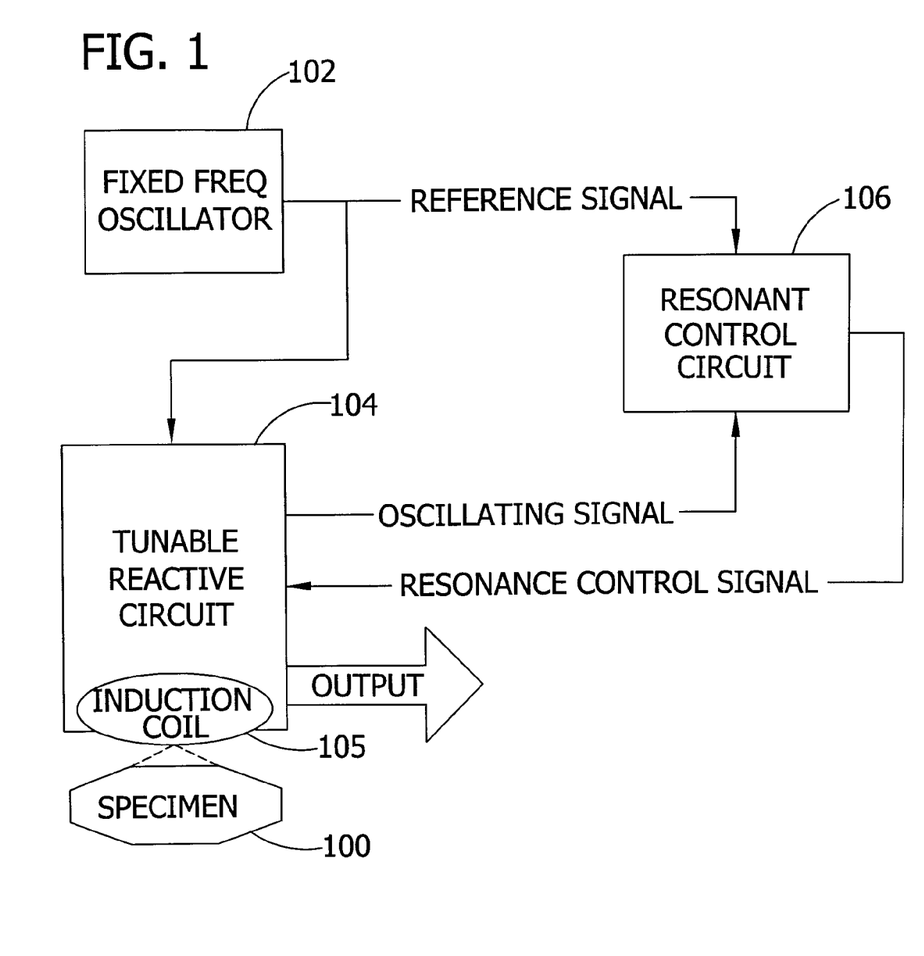
FIG. 1 is a block diagram of one embodiment of the invention.

In one form, the invention comprises an apparatus for measuring a condition (e.g., conductivity) of a specimen 100, such as human tissue, as illustrated in FIG. 1. A fixed frequency oscillator 102 provides a fixed frequency reference signal having a phase. An induction coil of a tunable reactive circuit 104, such as a series RLC circuit, is driven by the reference signal of the oscillator 102. The fixed frequency oscillator 102 is independent of and isolated from the tunable reactive circuit 104. The circuit 104 includes an induction coil 105 adapted to be positioned adjacent the specimen 100. The circuit 104 generates an oscillating signal corresponding to the condition of the specimen 100. In other words, the proximity of the specimen 100 to circuit 104 affects the point of resonance of the reactive circuit, such as by modifying the impedance of the reactive circuit.

A resonant control circuit 106 compares the reference signal to the oscillating excitation signal and provides to the tunable reactive circuit 104 a resonance control signal representative of the comparison. The resonance control signal tunes the tunable reactive circuit 104 so that resonance is maintained while the frequency of the oscillating signal is substantially constant. As will be discussed below, the tunable reactive circuit 104 provides an output signal having a parameter indicative of the condition of the specimen 100.

Thus, in one embodiment, the invention comprises a method for measuring the condition of the specimen 100. The coil of the tunable reactive circuit 104, driven by the reference signal of the oscillator 102, is positioned adjacent the specimen 100. The oscillating signal corresponding to the condition of the specimen 100 is generated by the tunable circuit 104 so that the output signal has a parameter indicative of the condition of the specimen 100. The reference signal is compared to the oscillating signal by the resonant control circuit 106. The tunable reactive circuit 104 is kept tuned to resonance by the resonant control circuit 106 while the oscillating signal maintains a substantially constant frequency.

Figure 2:
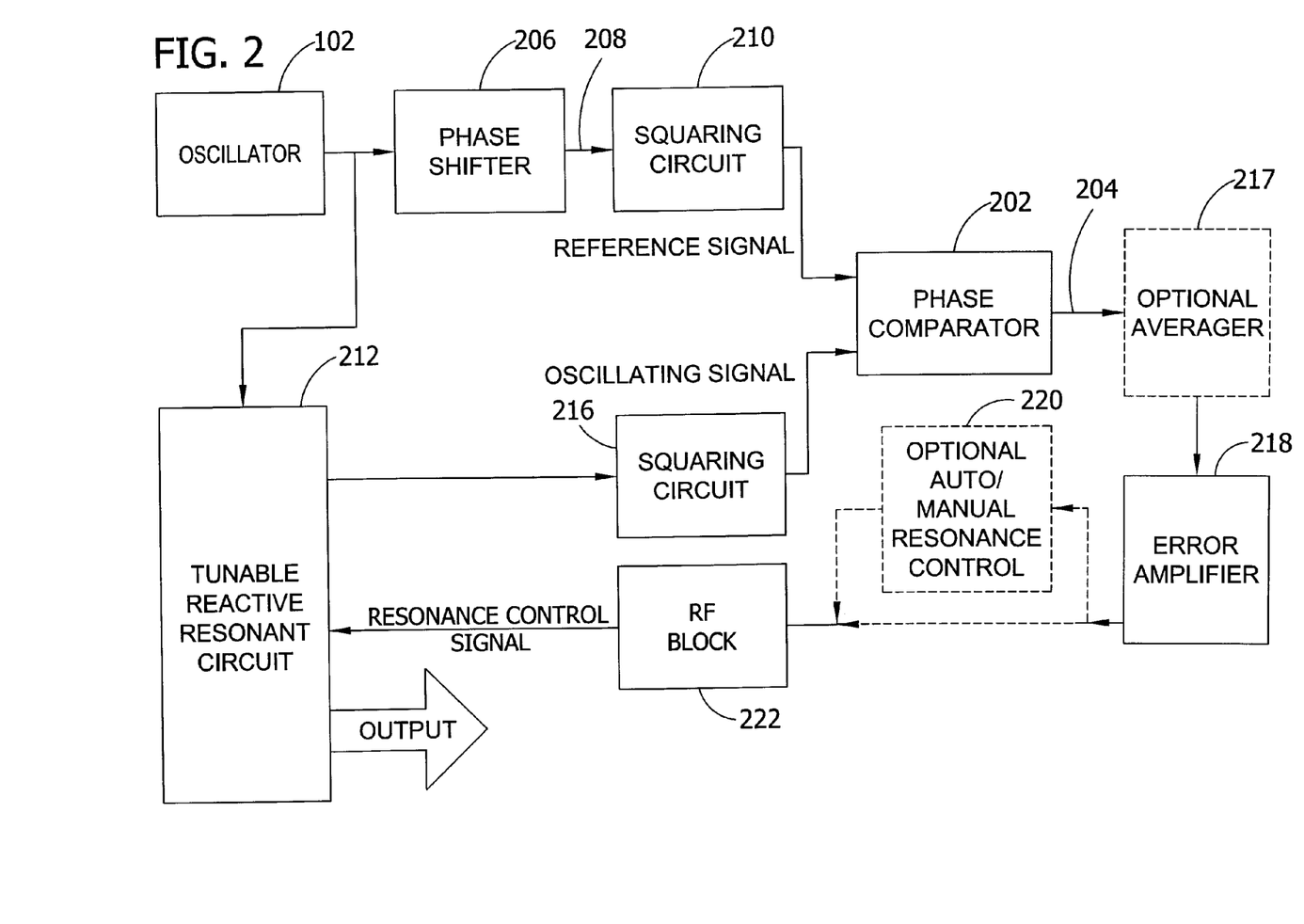
FIG. 2 is a block diagram of another embodiment of the invention.

As illustrated in the embodiment of FIG. 2, the resonant control circuit 106 compares the phase of the reference signal to the phase of the oscillating signal. The resonant control circuit includes a phase comparator 202 having first and second inputs and yielding a phase difference signal 204 indicative of a phase difference of signals applied to the first and second inputs. A phase shifter 206 shifts the phase of the oscillating signal of the oscillator to provide a shifted signal to a first squaring circuit 210 for squaring the shifted signal, this providing the reference signal to the first input of the phase comparator 202. In the embodiment of FIG. 2, the tunable reactive circuit 104 comprises a tunable reactive resonant circuit 212 such as a series RLC circuit providing a resonant output signal 214. A second squaring circuit 216 squares the resonant output signal 214 to generate the oscillating square wave signal provided to the second input of the phase comparator.

The phase difference signal, which may be averaged by an optional averager 217 (e.g., an integrator) is provided to an error amplifier 218 which is responsive to the phase difference signal 204. The error amplifier 218 provides the resonance control signal to the tunable reactive resonant circuit 212. In general, the resonance control signal varies one or more of the parameters of the tunable reactive resonant circuit 212 in order to maintain the resonance of the circuit 212 at a substantially constant frequency.

Optionally, an automatic or manual resonance control circuit 220 may be used for selectively providing the resonance control signal to the tunable circuit 212. In one embodiment, the control circuit 220 has a first mode and a second mode. In the first mode, the resonance control signal is provided to the tunable circuit 212 substantially continuously. In the second mode, the resonance control signal is provided to the tunable circuit 212 intermittently in response to operator input, as noted in more detail below. In addition, an rf blocking circuit 222, such as an rf choke in line together with a bypass capacitor between error amplifier 218 and the tunable circuit 212, may be employed.

In general, in one embodiment, the condition of the specimen being measured is conductivity indicative of at least one of the following: hypothermia; hyperthermia; circulatory performance; cardiac output; arterial dilation; edema; and fat distribution.

Figure 3:
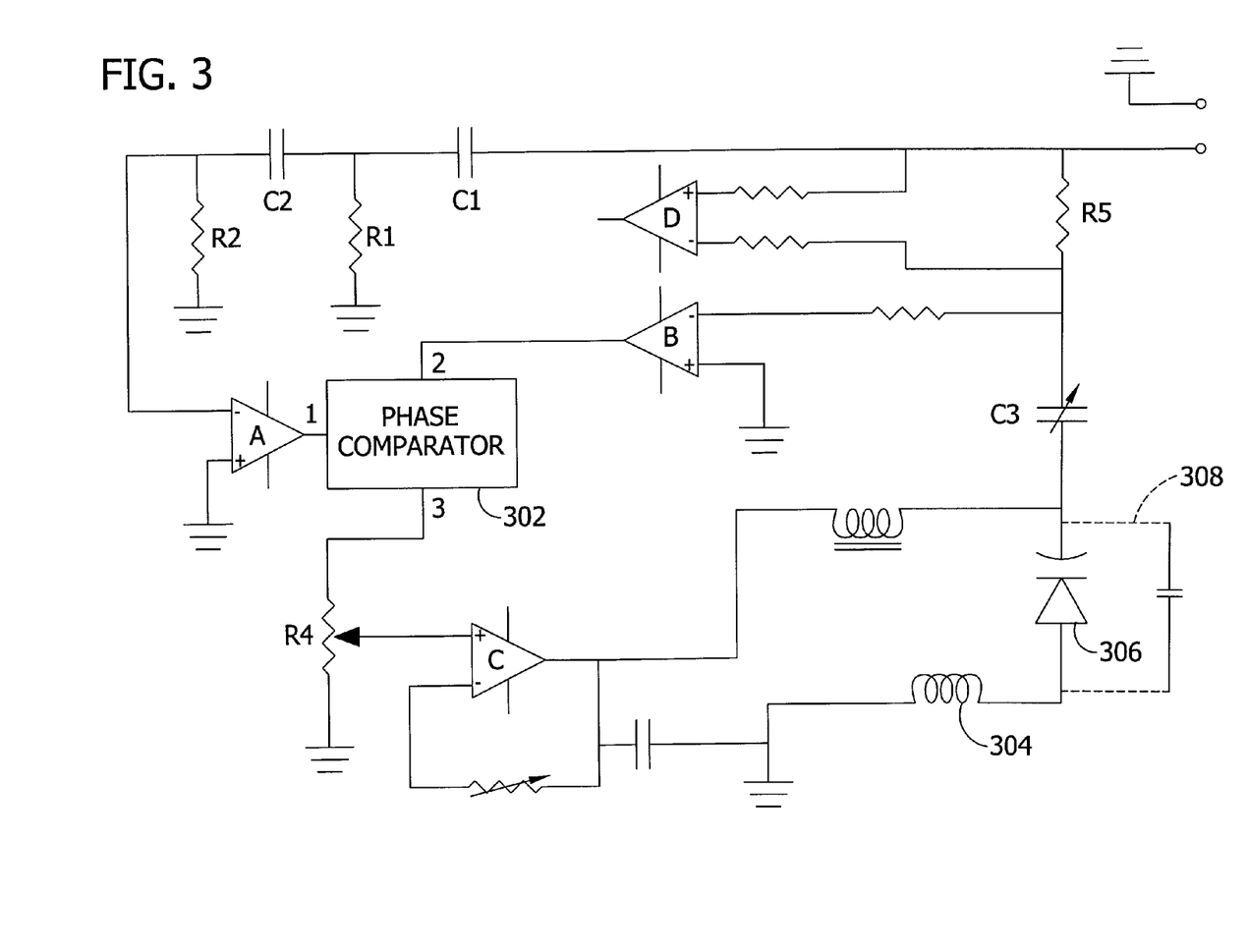
FIG. 3 is a schematic diagram of one embodiment of the invention.

FIG. 3 is a schematic of the electronic components comprising an RLC circuit maintained in a resonance condition according to one embodiment of the invention. The schematic indicates functionality and describes an example of a working circuit. Insignificant details have been omitted for clarity. In one embodiment, resistor R5 is about 10 ohms, since the resistance appearing due to eddy currents will be in that vicinity. However, to achieve a resonance locked condition due to circuit variations, resistor R5 may have a value as high as 1000 ohms.

Signals arriving at pins 1 and 2 of phase comparator 302 are shaped into square wave pulse trains by voltage comparators A and B. If the RLC circuit comprised of probe coil 304, varactor 306, resistor R5 and capacitor C3 is at resonance, then the signal arriving at pin 2 of comparator 302 leads the signal at pin 1 by 90 degrees—this is ensured by the phase shift network made up of resistor R1, capacitor C1 and resistor R2, capacitor C2.

If the inductance of the probe coil 304 rises when it is placed adjacent a specimen, then resonance would be lost and the signal at pin 2 of comparator 302 would lead pin 1 by more than 90 degrees. However, this difference in phase is indicated at pin 3 of the phase comparator 302. As a result, amplifier C increases the DC voltage applied to the varactor 306, reducing its capacitance. A reduction in varactor capacitance tends to restore the 90 degree phase shift.

Alternatively, if inductance were to fall when the coil 304 is placed adjacent a specimen, resonance would again be lost causing the signal at pin 2 to lead pin 1 by less than 90 degrees. This condition causes amplifier C to lower the DC voltage applied to the varactor 306, having the effect of increasing its capacitance, causing the 90 degree phase shift condition between pins 1 and 2 to be restored. Thus, the frequency of the excitation voltage applied to the RLC circuit remains substantially constant even as the voltage applied to varactor 306 varies. As a result, measurement of the variation of the voltage applied to the varactor 306, or preferably the voltage drop across the resistance contained in the RLC circuit, is one indication of condition (e.g., conductivity) of the specimen.

Difference amplifier D measures the voltage drop across the resistor R5, and is in proportion to the condition of the specimen. If impedance at resonance were to fall, current rises causing a larger voltage to appear across R5. Thus, increased impedance corresponds to a decreased voltage across R5.

Thus, the invention provides for a compact, inexpensive device that can be used in a variety of ways to evaluate cardiovascular health of a specimen via conductivity. In order to improve sensitivity and linearity, the probe coil 304 which is part of the tunable reactive circuit 104, 212 is placed at the surface of the specimen 100. The probe coil 304 is connected in series with the varactor type diode 306 to form a resonant LC circuit which can be auto-tuned by the resonant control circuit 106 to maintain resonance at all times. To aid stability of auto-tuning, the varactor 306 may be padded by introducing an optional, small mica capacitor 308 in parallel with the varactor 306. The varactor 306, which is a solid state device whose capacitance can be varied, is reverse biased in proportion to the phase angle difference between current through and voltage applied to the RLC circuit. If maintained at resonance, then the impedance of the RLC circuit varies linearly with specimen conductivity and at least quadratically with specimen dimensions.

In the case of a solenoidal coil surrounding a cylindrical specimen of diameter 2a, the resonant impedance Z when the coil is in series with an external resistor R and capacitance C, has a simple form, with impedance linearly related to specimen conductivity σ and magnetic permeability μ, as indicated by equation 1:

$$Z_{res} = R + \frac{1}{8} \frac{a^2 \mu \sigma}{C} \tag{1}$$

This result shows that impedance is linearly related to tissue conductivity, which is about 0.5 mho/m, and also linearly related to the magnetic permeability, which for human tissues is nearly identical with that of a vacuum. Sensitivity is improved when specimen diameter is increased (note the quadratic dependence on diameter indicated by equation 1), but also is improved if a smaller capacitance is used (equivalent to raising the resonant frequency).

For the case of a flat, circular loop coil of diameter 2a containing N turns of wire, the resonant impedance, when the loop is placed in the vicinity of a conductive sphere of radius b placed on the loop axis, is given by an equally simple form indicated by equation 2:

$$Z_{res} = R + \pi \sigma \omega^2 \mu^2 N^2 \frac{a^4 b^5}{30 R_c^6} \tag{2}$$

In this case, impedance is still linearly related to conductivity, but more sensitive to the conductive specimen's dimensions, here a sphere of radius b. Angular frequency is given by ω while the distance from the sphere center to any point on the current loop is $R_c$. The additional impedance due to eddy current generation is proportional to b raised to the fifth power, which permits the technique to be applied to cases where the dimensions of the conductive object may change.

Figure 4:
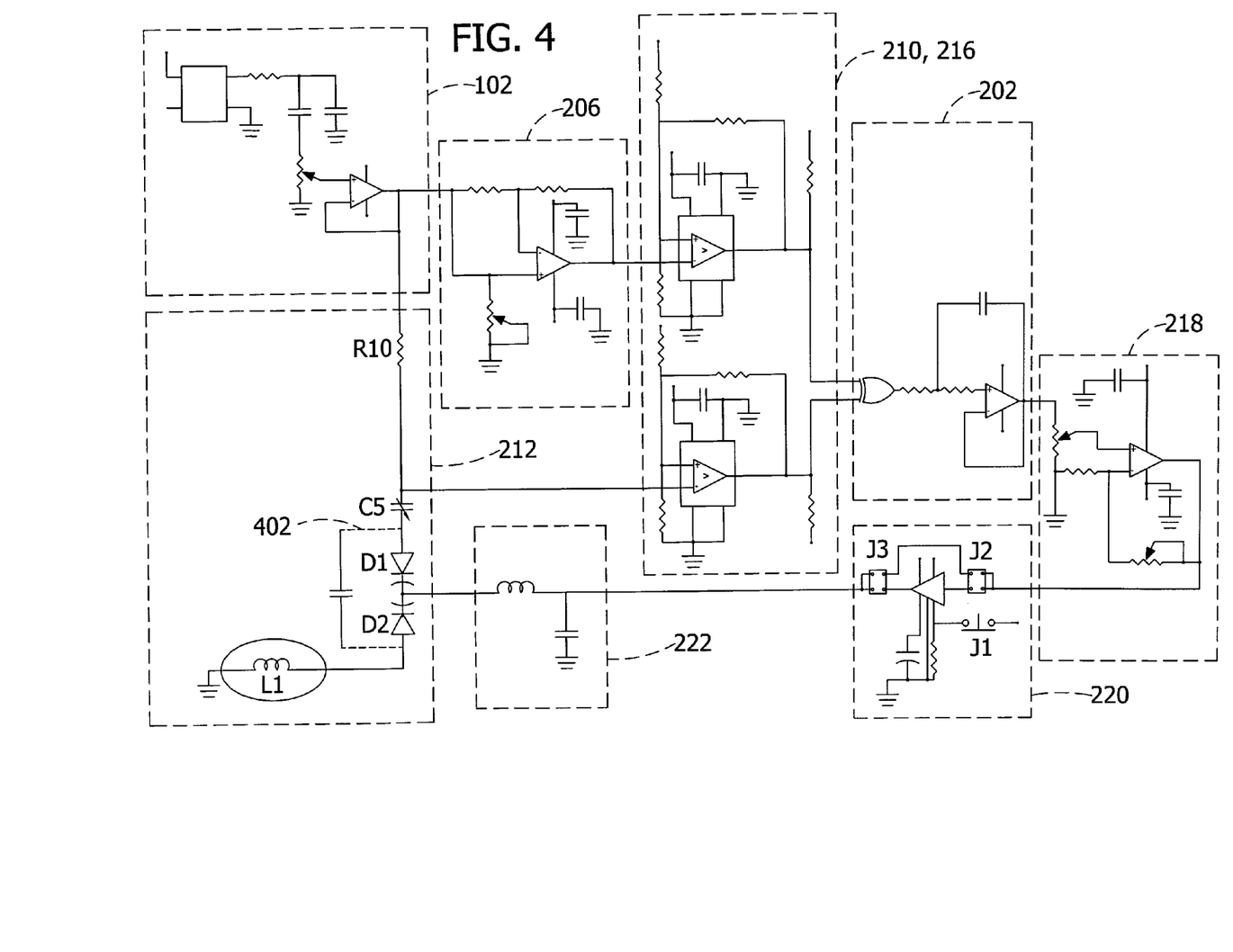
FIG. 4 is a schematic diagram of one embodiment of the invention, corresponding to FIG. 2.

FIG. 4 is a schematic diagram of one embodiment of the invention, corresponding to FIG. 2. In this embodiment, the optional auto/manual resonance control circuit 220 comprises a sample and hold circuit U8 activated by a manual switch J1 responsive to an operator input. Jumpers added to headers J2 and J3 selectively bypass the sample and hold circuit U8. The optional auto/manual resonance circuit 220 allows the user to select whether the tunable reactive circuit 212 is constantly held at resonance or whether pushbutton J1 will force the reactive circuit 212 to resonance each time it is depressed. To select between the two modes of operation, jumpers are added to headers J2 and J3 either to jumper row 1 for auto or to jumper row 2 for manual. In FIG. 4, the tunable reactive resonant circuit 212 comprises a varactor D1 and D2 and a resistor R10 in series with a sensor coil L1. As noted above, an optional padding capacitor 402 in parallel with the varactor D1, D2 may be provided. As illustrated, an rf blocking circuit 222 is in line between the resonance control circuit 220 and the varactor D1, D2. In this embodiment, the voltage across resistor R10 comprises the parameter indicative of the condition of the specimen so that resistor R10 is the component of the RLC circuit which is monitored.

Application to Hypothermia and Hyperthermia

When body temperature has dropped to dangerously low levels, blood circulation into the extremities is reduced—i.e., hypothermia. Thus, blood volume, for example, would be reduced in any of the patient's fingers. Furthermore, the temperature of body tissues in the area of reduced blood flow is reduced, resulting in a drop of specific conductivity. As indicated by equation 1, impedance at resonance is decreased due to the drop in conductivity, but is especially affected by a reduction in blood volume—note that impedance responds to the square of the specimen radius, which presumably is a function of blood volume and capillary dilation.

Using a sensor in the form of a solenoid type induction coil according to the invention (e.g., probe coil 304 or sensor coil L1 of FIG. 4), the effectiveness of any approach to treat hypothermia may be continuously monitored by placing the coil directly over a finger (e.g. the index finger). As blood flow returns to the extremities and blood becomes warmer, impedance in the RLC circuit, of which the coil is part, increases and eventually levels off. It is important to note that this type of measurement has the ability to probe tissues well beneath the skin surface, which is something that a non-implanted thermistor is unable to do accurately and consistently.

Likewise, the onset of hyperthermia is something that may be monitored with a conductivity sensor of the solenoid type, if placed around a finger, or perhaps even the ankle of the wearer. Given the simplified electronics design of the "resonant locked" device of the invention, the sensor may be compact and unobtrusive. In one form, data would be accessed remotely using RF telemetry. As temperature rises, blood flow into the probed tissue rises as well. Thus, the signal from either the solenoid or flat coil type sensor rises accordingly. Given the availability of appropriate mathematical forms derived for either of these coil types, calibration may be unnecessary and absolute assessments are feasible provided some correlation is developed between body temperature and blood volume in the target tissues.

Circulatory Performance

In some cases, it may be desirable to assess the robustness of the human circulatory system. This may be achieved by deliberately plunging a subject's hand into an ice water bath for a specified period of time, followed by removal and placement of a solenoid type inductive sensor according to the invention over the index finger for monitoring. Subsequently, the signal produced by the sensor coil would track the reestablishment of normal conditions. Recovery of normal blood flow and temperature for someone having healthy circulation is expected to be different from one whose circulatory system is impaired in some way. The transient signal produced by the sensor coil during the course of return to normal blood flow and temperature may be analyzed by spectral deconvolution to identify the time constants associated with the overall process or a much simpler approach may be employed, if warranted.

Cardiac Output

An EKG provides useful information about the electrical signals associated with a beating heart. However, it may not produce significant information about output on each beat. By placing a loop coil according to the invention, having dimensions similar to that of the heart, at a location just above the heart, a pulsating signal appears as the heart undergoes expansion and contraction through each beat. An RLC circuit equation 3 can be developed for the coil, replacing the current I with a harmonically varying current i(t):

$$\varepsilon = i(t)R + L\frac{di}{dt} + N^2\frac{d\Phi_e}{dt} + \frac{1}{C}\int_0^t i(\tau)d\tau \tag{3}$$

The inductance of the isolated coil of N turns is given by L. Taking the time derivative of equation 3, and dividing by $j\omega$ leads to an impedance Z as indicated by the following equation 4:

$$Z = R + \pi\sigma\omega^2\mu_0^2 N^2 \frac{a^4 b^5}{30 R_c^6} + j\left(L\omega - \frac{1}{\omega C}\right) \tag{4}$$

Of course, there are higher order corrections to both real and imaginary parts of Z, but these are not important for most cases. To arrive at approximately a 6.0 ohm contribution, due to eddy currents, we would need about N=50 for a multi-turn loop coil of diameter 4.0 cm, assuming further that $a=b=R_c$ and a frequency of 10 MHz.

Clearly, the eddy current contribution to impedance will be very sensitive to the size of the conductive object, a feature which can be put to good use. Comparison with the solenoid result suggests that the flat multi-turn loop coil is more sensitive to specimen size. It also seems that adequate sensitivity for the flat loop coil may be more difficult to achieve than for the solenoid. The advantage of the flat loop coil, however, is that it can easily and conveniently be placed into close contact with various body surfaces. In either case, sensitivity is adequate to allow measurement.

As equation 4 indicates, coil impedance at resonance varies with the fifth power in heart diameter—considering the heart as though it were a sphere. The reason for expecting a fluctuating signal is that the blood is concentrated in the heart to a much greater extent than in tissues immediately surrounding the heart. Thus, the development of eddy currents is greatly reduced as the heart becomes greatly contracted. A model of heart volume as it goes through the expansion and contraction cycle, together with heart tissue conductivity data, coil dimensions and placement, allows simulation of the expected signal produced by an induction coil sensor. Adjusting the volume change until the simulated signal compares favorably with the actual signal may lead to a measurement of the actual volume change per beat—depending on the accuracy of equation 4.

Arterial Dilation

An application similar to evaluation of cardiac output involves the placement of a relatively small diameter induction coil according to the invention directly over a site where a significant artery runs sufficiently close to the body surface. An excellent example would be the radial artery in the wrist, where pulse rate is commonly determined. As indicated by MRI cross sections of the wrist (not illustrated), the radial artery is very close to the skin surface and sufficiently large that an inductive sensor registers a periodic signal in response to arterial expansion and collapse. While other methods attempt to assess arterial performance using various types of pressure transducers, which would only provide data about pulse strength, the induction coil sensor according to the invention provides a direct measure of the dilatational response of the probed artery to a pressure pulse emanating from the heart.

Fat Distribution

The induction coil sensor may be used as a diagnostic for distribution of body fat, especially abdominal fat. Belly fat, and visceral fat in particular, are excellent indicators for heart disease and diabetes. Visceral fat is fat which is located more deeply in the abdominal cavity and is usually associated with internal organs.

Since fatty tissue is much less conductive than muscle or other tissues, it would be possible to use multi-turn loop coils to obtain a 2-d map of conductivity across the abdominal surface. As theory has shown, the depth of field of the conductivity measurement may be controlled by using coils of different diameters—larger diameter coils probing more deeply. Thus, with use of different diameter coils, both 2-d and 3-d imaging of fat is feasible.

Other Embodiments and Applications

The applications discussed above are exemplary and not exhaustive. In some cases, a number of coils may be implemented, with some serving the purpose of inducing the eddy currents while others passively sense the fields created by the eddy currents. One application using multiple coils may be used to evaluate the appearance of edema in brain tissues due to injury or disease. This would be an appropriate application of the invention since the collection of conductive fluids in any body tissue would likely produce an abnormally high electrical impedance.

It is also contemplated that the circuitry of the invention may be implemented digitally. For example, referring to FIG. 1, the reference signal and oscillating signal may be applied to an analog to digital converter and digitally processed to generate a digital signal which may be applied to a digital to analog converter to generate the resonance control signal. Also, the output may be converted to a digital signal and digitally processed to determine its indications.

Figure 5:
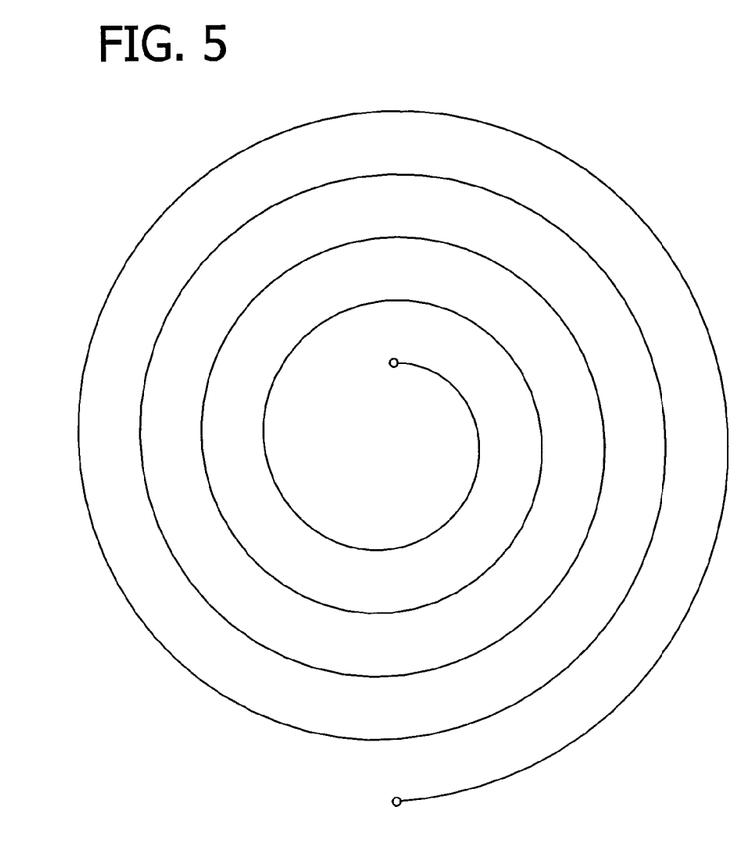
FIG. 5 is a plan view of one embodiment of an induction coil of the invention having a spiral configuration.

Though there are coil designs such as the solenoid or the multi-turn loop, many other possibilities exist. A particular useful variation of the multi-turn type is a coil whose subsequent turns gradually increase coil diameter by the diameter of the wire used. For example, as illustrated in FIG. 5, a flat, spiral-wound induction coil may be employed as part of the invention as the spiral configuration tends to provide added sensitivity. Subsequent turns will be added in an outward spiraling manner which increases the diameter, but allows the thickness or height of the coil to remain constant, equal to the diameter of the wire used. The leads to the coil are at the start of the first turn (i.e. the center of the coil) and at the end of the last turn (i.e. the outer edge of the coil). The overall diameter of the coil can be expressed with the following equation:

$$d_{coil} = 2Nd_{wire} + d_{hole}$$

Where N is the number of turns in the coil, $d_{wire}$ is the physical diameter of the wire being used to construct the coil, and $d_{hole}$ is the diameter of the hole in the center of the coil. The completed coil is able to lie flat, inasmuch as all turns lie in the same plane, with a height equal to the wire diameter.

With regard to the phase detection circuitry, the output of the phase comparator is a square wave. There are a number of techniques that could be used to convert this square wave into a dc value that represents phase error. One alternative technique involves simply taking the average of the square wave (e.g., see FIG. 2 and optional averager 217). The simple average of a waveform is given by:

$$V_{avg} = \frac{1}{T}\int_0^T V(t)dt$$

In one embodiment, a filter may be applied to the output of an integrator to get a running average over several waveform periods. The resulting voltage can then provide the needed feedback to retune the RLC circuit via the varactor.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A noninvasive apparatus for measuring a condition of a specimen comprising:

A noninvasive oscillator providing a reference signal having a phase and a fixed frequency;

A noninvasive tunable reactive circuit receiving the reference signal from the oscillator, said tunable reactive circuit containing an induction coil adapted to be positioned on a surface of the specimen and connected in series with a varactor type diode to form an RLC circuit and generating an oscillating signal corresponding to the condition of the specimen, said oscillating signal having a frequency and having a phase, said tunable reactive circuit providing an output signal having a parameter indicative of the condition of the specimen, wherein the parameter comprises an impedance of an element of said tunable reactive circuit, the impedance linearly relating to a conductivity of the specimen; and A noninvasive resonant control circuit comparing the reference signal to the oscillating signal and providing to the tunable reactive circuit a resonance control signal representative of the comparison, said resonance control signal tuning the tunable reactive circuit to resonance at the fixed frequency of the oscillator while the impedance of the element of said tunable reactive circuit is measured.

2. The apparatus of claim 1 wherein the resonant control circuit compares the phase of the reference signal to the phase of the oscillating signal and wherein the parameter corresponds to a voltage across a component of the tunable reactive circuit.

3. The apparatus of claim 2 wherein the resonant control circuit comprises:

a phase comparator having first and second inputs and providing a phase difference signal indicative of a phase difference of signals applied to the first and second inputs;

a phase shifter shifting the phase of an oscillating signal of the oscillator to provide a shifted signal;

a first squaring circuit for squaring the shifted signal to provide the reference signal to the first input of the phase comparator;

a second squaring circuit for squaring a resonant output signal of the tunable reactive circuit to provide the oscillating signal to the second input of the phase comparator; and, an error amplifier responsive to the phase difference signal for providing the resonance control signal to the tunable reactive circuit.

4. The apparatus of claim 3 wherein the tunable reactive circuit comprises a series RLC circuit.

5. The apparatus of claim 4 wherein the RLC circuit comprises a fixed resistance.

6. The apparatus of claim 5 further comprising a padding capacitor in parallel with the varactor.

7. The apparatus of claim 4 wherein the resonant control circuit further comprises an averager averaging the phase difference signal and providing the averaged phase difference signal to the error amplifier.

8. The apparatus of claim 1 further comprising a control circuit for selectively providing the resonance control signal to the tunable reactive circuit, said control circuit having a first mode and a second mode, wherein in the first mode the resonance control signal is provided to the tunable reactive circuit substantially continuously and wherein in the second mode the resonance control signal is provided to the tunable reactive circuit intermittently in response to operator input.

9. The apparatus of claim 8 wherein the control circuit comprises a sample and hold circuit activated by a manual switch responsive to the operator input and jumpers for selectively bypassing the sample and hold circuit.

10. The apparatus of claim 1 wherein the condition is at least one of the following: hypothermia; hyperthermia; circulatory performance; cardiac output; arterial dilation; edema; and fat distribution.

11. The apparatus of claim 1, wherein impedance at resonance is further decreased due to a drop in blood volume.

12. A noninvasive apparatus for measuring a condition of a specimen comprising:

a noninvasive oscillator providing a reference signal having a phase and a fixed frequency;

A tunable reactive circuit receiving the reference signal from said oscillator, the reference signal inducing a resonance condition at a resonant frequency within said tunable reactive circuit, said tunable reactive circuit containing an induction coil adapted to be positioned on a surface of the specimen and connected in series with a varactor type diode to form an RLC circuit and generating an oscillating signal corresponding to a condition of the specimen, said tunable reactive circuit providing an output signal having a parameter indicative of the condition of the specimen, wherein the parameter comprises an impedance of an element of said tunable reactive circuit, the impedance linearly relating to a conductivity of the specimen; and a noninvasive resonant control circuit comparing the reference signal to the oscillating signal and providing to said tunable reactive circuit a resonance control signal representative of the comparison, the resonance control signal maintaining the resonant frequency of said tunable reactive circuit at the same frequency as said oscillator so that the impedance of said tunable reactive circuit element is measured under a condition of resonance.

13. A method for measuring a condition of a specimen comprising:

positioning on a surface of the specimen a noninvasive apparatus comprising a tunable reactive circuit connected in series with a varactor type diode to form an RLC circuit, the tunable reactive circuit receiving a fixed frequency reference signal from an oscillator;

generating, from the noninvasive apparatus, an oscillating signal corresponding to the condition of the specimen, said oscillating signal having a frequency and having a phase;

providing, from the noninvasive apparatus, an output signal having a parameter indicative of the condition of the specimen;

comparing the reference signal to the oscillating signal; and controlling the tunable reactive circuit so that the tunable reactive circuit remains in resonance at the fixed frequency of the oscillator while an impedance of the tunable reactive circuit is measured.

14. The method of claim 13 wherein the condition is at least one of the following: hypothermia; hyperthermia; circulatory performance; cardiac output; arterial dilation; edema; and fat distribution.

15. The method of claim 13 wherein comparing comprises comparing the phase of the reference signal to the phase of the oscillating signal and wherein the parameter is a voltage across a component of the tunable reactive circuit.

16. The method of claim 15 wherein comparing comprises averaging a phase difference signal and providing the averaged phase difference signal to an error amplifier for controlling the resonance of the tunable reactive circuit.

17. The method of claim 13 further comprising selectively providing a resonance control signal to the tunable reactive circuit, wherein in a first mode the resonance control signal is provided to the tunable reactive circuit substantially continuously and wherein in a second mode the resonance control signal is provided to the tunable reactive circuit intermittently in response to operator input.

18. The method of claim 13 wherein the parameter comprises an impedance of an element of the tunable reactive circuit, said impedance linearly relating to a conductivity of the specimen.

19. The method of claim 13 further comprising using the output signal, measuring a volume change per beat of a heart.

* * * * *